US007872743B2

(12) United States Patent
Taniguchi et al.

(10) Patent No.: US 7,872,743 B2
(45) Date of Patent: Jan. 18, 2011

(54) DEFECT INSPECTION SYSTEM

(75) Inventors: Koichi Taniguchi, Hitachinaka (JP);
Yuzo Morita, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 213 days.

(21) Appl. No.: 12/335,173

(22) Filed: Dec. 15, 2008

(65) Prior Publication Data

US 2009/0161095 A1 Jun. 25, 2009

(30) Foreign Application Priority Data

Dec. 19, 2007 (JP) ............................. 2007-327816

(51) Int. Cl.
*G01N 21/00* (2006.01)
(52) U.S. Cl. ................................ 356/237.4; 356/237.6
(58) Field of Classification Search ... 356/237.1–241.6, 356/242.1–243.8, 426–431, 600–640
See application file for complete search history.

(56) References Cited

U.S. PATENT DOCUMENTS

| 6,797,975 | B2 * | 9/2004 | Nishiyama et al. | ..... 250/559.04 |
| 7,339,661 | B2 * | 3/2008 | Korngut et al. | .......... 356/237.2 |
| 7,528,942 | B2 * | 5/2009 | Nakano et al. | ............ 356/237.3 |
| 2006/0290923 | A1 | 12/2006 | Nakano et al. | |
| 2007/0182958 | A1 * | 8/2007 | Manabe et al. | ............ 356/237.2 |

FOREIGN PATENT DOCUMENTS

| JP | 5-218163 | 8/1993 |
| JP | 6-258239 | 9/1994 |
| JP | 3566589 | 9/2004 |
| JP | 2007-033433 | 2/2007 |
| JP | 2007-107960 | 4/2007 |

\* cited by examiner

*Primary Examiner*—Gregory J Toatley
*Assistant Examiner*—Jarreas C Underwood
(74) *Attorney, Agent, or Firm*—McDermott Will & Emery LLP (57) ABSTRACT

In a defect inspection system using a plurality of detectors such as an upright detector and an oblique detector, if illumination light and wafer height are adjusted to the detection field of view of one detector, a defocused image is detected by other remaining detectors, resulting in degradation of the detection sensitivity. The present invention solves this problem.

When a plurality of detectors such as an upright detector and an oblique detector are used in the defect inspection system, the reduction of the inspection sensitivity can be prevented by correcting the field positions of the other remaining detectors with respect to the field of view of the one detector. Further, the variation in optical axis for each inspection system due to the variation in parts and assembly errors can be reduced.

6 Claims, 5 Drawing Sheets

DEFECT INSPECTION SYSTEM

BACKGROUND OF THE INVENTION

1. Field of the Invention

The present invention relates to a defect inspection system which inspects a defect such as a particle in an object under inspection, and particularly to a defect inspection system suitable for inspection process of a substrate with a pattern, such as a semiconductor wafer, liquid crystal display, and the like.

2. Description of the Related Art

If particles are present on the surface of a substrate in the process of manufacturing a semiconductor device, liquid crystal display, or the like, failures such as short circuit and inferior insulation will take place therein. Causes by which particles are generated include dust that occurs from equipment, the human body, and process gas and other materials.

With the increasing miniaturization in semiconductor process, the minuteness of a defect that will cause failures is also remarkable and accordingly defect detection with higher accuracy is requested.

Recent years have seen a trend of an increase in the use of multilayer wafers because of higher integration of semiconductors. A multilayer wafer is manufactured by repeating a process of forming a transparent thin film such as an oxide film on a substrate and a process of forming a circuit pattern on the film. For this reason, the need for detection of particles and defects on the surface of the transparent thin film has been important in the field of defect inspection on a wafer.

In order to meet this demand, JP-A-2007-107960 discloses a technique for reducing scattered light from a transparent thin film base pattern using a low-elevation-angle detector in addition to a detector installed in a direction perpendicular to the wafer, used in common dark-field inspection systems, to thereby improve the detection sensitivity.

Likewise, JP-A-2007-33433 also discloses a detection technique using a low-elevation angle as detection angle to reduce unevenness in brightness of scattered light from a wafer.

With the above-mentioned techniques, both a low-elevation-angle detector and a perpendicular detector can be used at the same time, thus enabling defect detection with high sensitivity using a plurality of defect signals.

SUMMARY OF THE INVENTION

However, when a wafer height is aligned with an illumination position with respect to an upright detector at the time of adjustment of a detection field of view, the focus of other remaining detectors is not illuminated possibly resulting in degradation of the detection sensitivity.

The present invention has been devised in view of the above-mentioned situation. The present invention provides a defect inspection system which, when a plurality of detectors are used, corrects a position at which a sensor is located and makes the focal positions of these detectors coincide with each other, thus preventing the detection sensitivity from degrading.

In order to solve the above-mentioned problem, the present invention includes a plurality of detectors having optical axes which are mutually different for a sample, wherein at least one detector is provided with a mechanism for correcting a position at which a sensor is located. The defect inspection system estimates an appropriate imaging position with respect to the wafer height and illumination position and moves the sensor to prevent the detection sensitivity from degrading. The sensor position may be corrected separately according to the magnification, illumination conditions, and the like.

For example, if the distance between the sample and the sensor is adjusted in one of the plurality of detectors, sensors of other remaining detectors are moved to correct imaging position shift.

According to one aspect of the present invention, a defect inspection system for inspecting a defect in a sample, the system comprises: a stage on which the sample is moved; an illumination optical system for irradiating a surface of the sample with a testing illumination light beam having a predetermined incident angle with respect to the sample surface to generate a beam spot on the sample surface; an oblique detector including a first sensor having a first optical axis inclined with respect to the sample surface by a predetermined angle to detect light from the beam spot, and a sensor movement device which moves the first sensor; an upright detector including a second sensor having a second optical axis along the normal of the sample surface to detect light from the beam spot; and a signal processor including a processing controller to detect a defect on the sample using outputs from the oblique detector and the upright detector. The processing controller controls the stage to move the sample in the second optical axis direction to adjust the focal length of the upright detector. The processing controller controls the sensor movement device according to the amount of movement of the sample to move the position of the first sensor in the oblique detector.

Preferably, the processing controller calculates the coordinate (xs1, zs1) of a defect in the xz coordinate system of the oblique detector using the following formulas:

$$xs1 = x0 \cdot \cos \beta + z0 \cdot \sin \beta$$

$$zs1 = -x0 \cdot \sin \beta + z0 \cdot \cos \beta$$

and controls the sensor movement device so that the first sensor is disposed at an imaging position associated with the coordinate (xs1, zs1) of the defect, where the coordinate of the defect before the sample is moved is (0, 0), the coordinate of the defect in the xz coordinate system of the upright detector is (x0, z0), the coordinate of the defect in the oblique xz coordinate system of the oblique detector is (xs1, zs1), and the oblique angle of the oblique detector is β.

Further features of the present invention will become apparent from detailed descriptions of the preferred embodiments and accompanying drawings.

The present invention makes it possible to use differences in focal positions of detectors as suitable light-receive conditions by correcting the position of a light-receive system, thus preventing the inspection sensitivity from degrading and accordingly attaining stable inspection.

Further, according to the present invention, the effects of correcting the variation in parts, assembly errors, etc. in each defect inspection system can be obtained.

BRIEF DESCRIPTION OF THE DRAWINGS

Other objects and advantages of the invention will become apparent from the following description of embodiments with reference to the accompanying drawings in which.

DESCRIPTION OF THE PREFERRED EMBODIMENTS

An embodiment of the present invention will be explained below with reference to the accompanying drawings. While the present embodiment is merely an example for attaining the present invention, it should be noted that the present embodiment does not limit the technical scope of the present invention. In each drawing, elements having the same function are assigned the same symbol.

(1) Configuration of the Defect Inspection System

Figure 1:
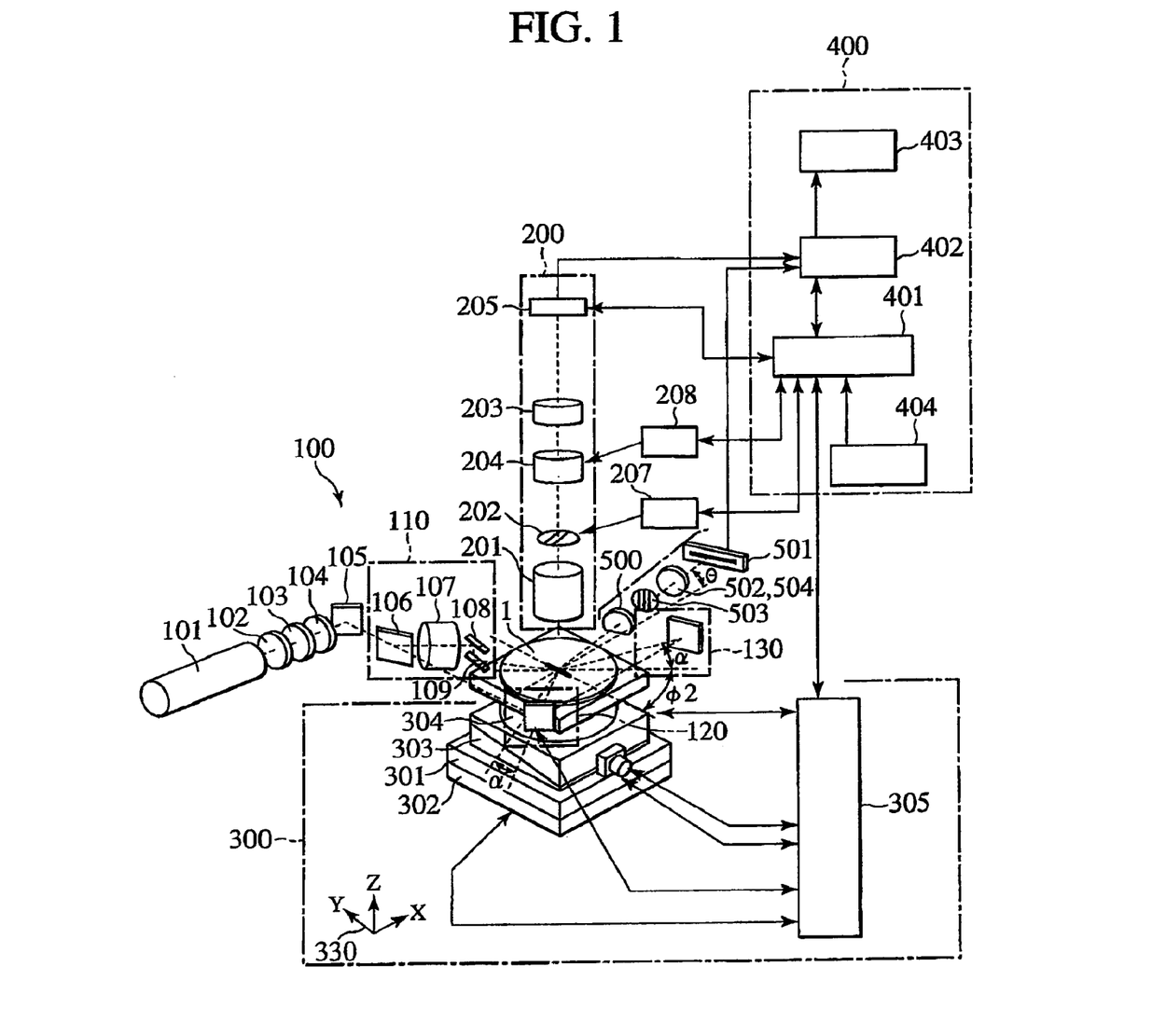
FIG. 1 shows the schematic configuration of a defect inspection system according to an embodiment of the present invention.

FIG. 1 shows the schematic configuration of the defect inspection system according to the embodiment of the present invention. Referring to FIG. 1, the defect inspection system includes: a stage system 300 which moves a sample such as a wafer in the x, y, and z directions and around the z axis; an illumination optical system 100 which irradiates the sample with a testing illumination light beam; an upright detector 200 which detects scattered light from the sample; an oblique detector 500 which detects scattered light from the sample; and a control system 400 which performs calculation processing, signal processing, and the like.

The stage system 300 includes an x stage 301, a y stage 302, a z stage 303, a rotation stage 304, and a stage controller 305.

The illumination optical system 100 includes a laser light source 101; a beam expander composed of a concave lens 102 and a convex lens 103; a beam trimming unit composed of an optical filter group 104 and a mirror 105; and three beam-spot imaging units 110, 120, and 130. The beam-spot imaging unit 110 includes an optical branch element (or mirror) 106, an illumination lens 107 having a conic curved surface, and mirrors 108 and 109. An optical filter group 104 includes an ND filter and a wavelength plate.

Although it is preferable to use the third harmonic (THG), having a wavelength of 355 nm, of high-power YAG laser as the laser light source 101, the wavelength is not necessary 355 nm, nor the laser light source 101 necessarily be YAG or THG. That is, the laser light source 101 may be Ar laser, nitrogen laser, He—Cd laser, excimer lasers, or the like.

The upright detector 200 includes a detection lens 201, a spatial filter 202, an imaging lens 203, a zoom lens group 204, a one-dimensional sensor (image sensor) 205, a spatial filter control 207, and a zoom lens control 208. The oblique detector 500 includes a one-dimensional sensor (image sensor) 501, an objective lens 502, a spatial filter 503, and an imaging lens 504. A one-dimensional sensor 205 may be a TDI (time delay integration) sensor.

The control system 400 includes a calculation and processing unit (processing controller) 401, a signal processing unit 402, an output unit 403, and an input unit 404. The calculation and processing unit 401 includes a CPU or the like to drive a motor or the like and control the coordinates and sensors. The signal processing unit 402 includes an A/D converter, a delayable data memory, a difference processing circuit which takes a difference between chip signals, a memory unit which temporarily stores the chip differential signal, a threshold value calculation and processing unit which sets a pattern threshold value, and a comparator circuit.

The output unit 403 stores a result of defect detection such as particle detection, and outputs or displays the result of defect detection. Using the input unit 404, a command and data from the user are input.

A coordinate system 330 is shown at the bottom left of FIG. 1, where the x and y axes are taken on a plane (xy plane) and the z axis is taken perpendicularly to the xy plane. In this case, the optical axis of the upright detector 200 is disposed along the z axis while the optical axis of the oblique detector 500 is disposed on the xz plane.

(2) Configuration of the Illumination Optical System

Figure 2:
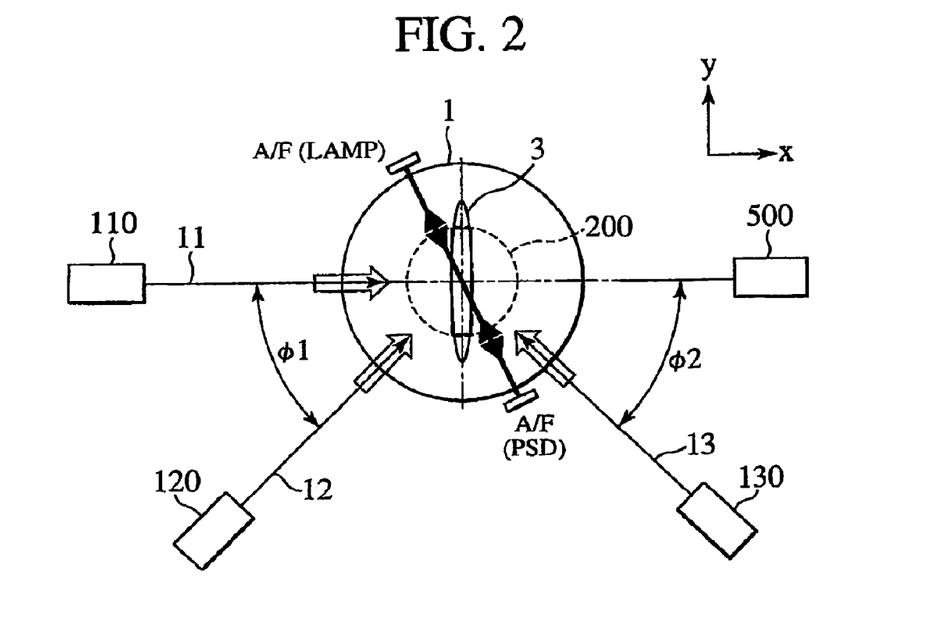
FIG. 2 explains three different testing illumination light beams generated by an illumination optical system of the defect inspection system.

Referring to FIG. 2, the three beam-spot imaging units 110, 120, and 130 of the illumination optical system 100 will be explained below with reference to FIG. 2. FIG. 2 shows a sample (substrate) 1 or a wafer viewed from the top. A testing illumination light beam 11 is irradiated in the x-axis direction through a first beam-spot imaging unit 110. A testing illumination light beam 12 is irradiated in a direction inclined with respect to the y axis by an angle of −45 degrees through a second beam-spot imaging unit 120. A testing illumination light beam 13 is irradiated in a direction inclined with respect to the y axis by an angle of 45 degrees through a third beam-spot imaging unit 130. An oblique detector 500 is disposed on the side opposite to the first beam-spot imaging unit 110.

The testing illumination light beams 11, 12, and 13 are obliquely irradiated forming a predetermined angle α with respect to the surface of the substrate (sample) 1. In particular, the amount of detected scattered light from a transparent thin film undersurface can be reduced by decreasing the elevation angle α of the testing illumination light beam 12 and 13.

These testing illumination light beams 11, 12, and 13 form an elongated beam spot 3 on the substrate (sample) 1. The beam spot 3 extends along the y-axis direction. The length of the beam spot 3 along the y-axis is larger than a detection field of view 250 of the one-dimensional sensor 205 of the upright detector 200.

The reason why the three beam-spot imaging units 110, 120 and 130 are provided in the illumination optical system 100 will be explained below. When the testing illumination light beams 12 and 13 projected on the xy plane form angles $\Phi1$ and $\Phi2$, respectively, with respect to the x axis, a condition $\Phi1=\Phi2=45$ is satisfied in the present embodiment. This makes it possible to prevent the 0th-order diffracted light from a non-repetitive pattern on the substrate 1 from being incident on the objective lens 201 of the upright detector 200. The reason is described in detail in U.S. Pat. No. 3,566,589 and therefore omitted herein.

The non-repetitive pattern on the substrate 1 is mainly composed of linear patterns formed in parallel and perpendicularly with each other. These linear patterns extend along the x- or y-axis direction. Since the patterns on the substrate 1 are protruded therefrom, a concave portion is formed between adjacent linear patterns. Therefore, the testing illumination light beams 12 and 13 irradiated from directions inclined with respect to the x and y axes, respectively, by an angle of 45 degrees are intercepted by protruded circuit patterns, and therefore a concave portion between linear patterns cannot be irradiated.

Therefore, the beam-spot imaging unit 110 is provided to generate the testing illumination light beam 11 which is along the x-axis direction. A concave portion between linear patterns can be irradiated with the testing illumination light beam 11, making it possible to detect a defect such as a particle existing the concave portion. Depending on the direction of linear patterns, the sample is rotated 90 degrees before inspection or the testing illumination light beam 11 is radiated in the y-axis direction.

When a light beam, for example the testing illumination light beam 11, is radiated in the x-axis direction onto a concave portion between linear patterns, it is necessary to intercept the 0th-order diffracted light so that the sensor may not detect the 0th-order diffracted light. The spatial filter 202 is provided for this purpose.

Figure 3A:
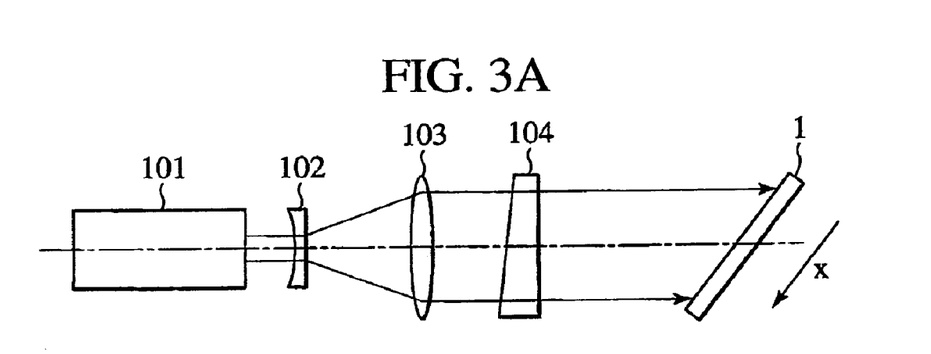
FIGS. 3A and 3B show an optical system which includes an illumination lens of the illumination optical system of the defect inspection system.
Figure 3B:
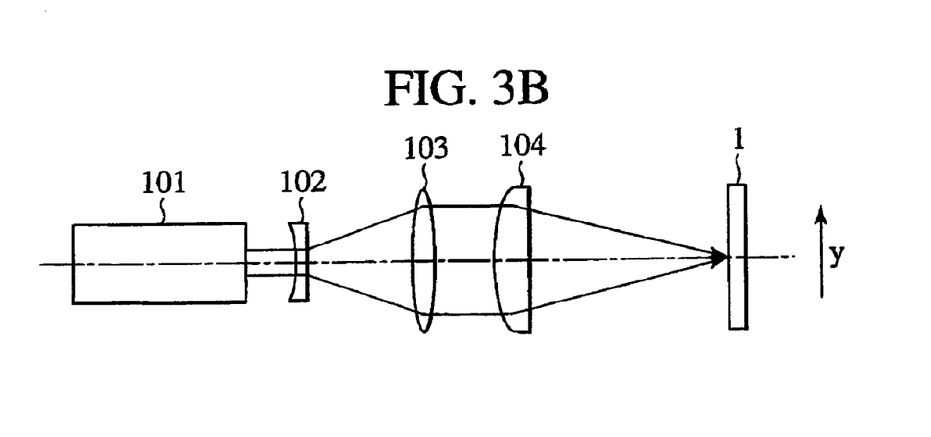
Figure 4:
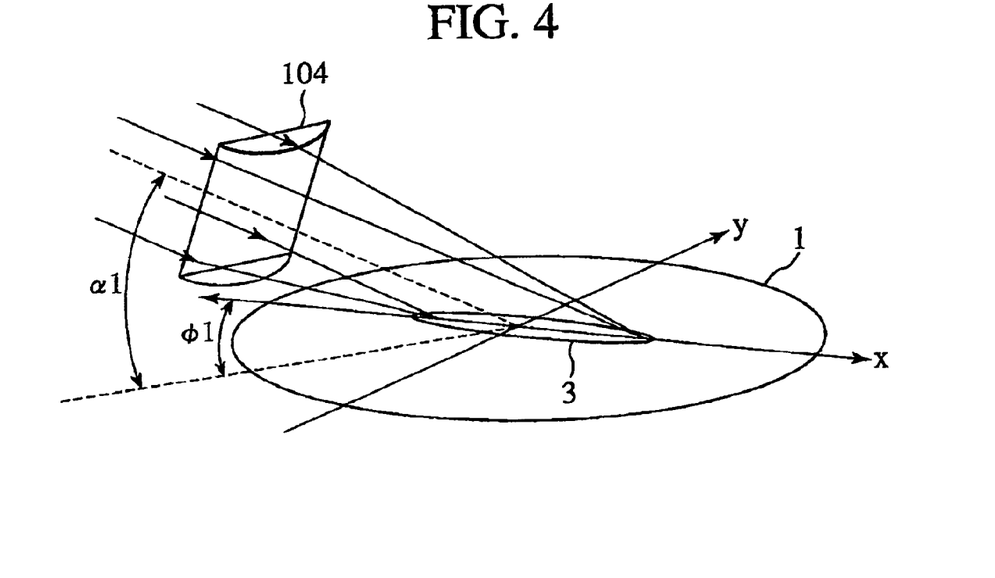
FIG. 4 shows the operation of the illumination lens of the illumination optical system of the defect inspection system.

A method for forming the elongated beam spot 3 will be explained below with reference to FIGS. 3A, 3B, and 4. FIGS. 3A and 3B show only the laser light source 101, the concave lens 102, the convex lens 103, and the illumination lens 104 of the illumination optical systems 100, and other components 105, 106, 107, 108, and 109 are omitted to facilitate understanding essential configuration.

The illumination lens 104 is a cylindrical lens having a conic curved surface, and the focal length linearly changes in the longitudinal direction, as shown in FIG. 3A. The illumination lens 104 has a cross section of a flat convex lens as shown in FIG. 3B. The illumination lens 104 can deflect in the y-axis direction even an illumination light beam obliquely incident on the substrate (sample) 1 to generate the slit-like beam spot 3 collimated in the x-axis direction, as shown in FIG. 4. The testing illumination light beam 11 forms an angle α1 with respect to the surface of the substrate (sample) 1. The testing illumination light beam 11 projected on the substrate (sample) 1 forms an angle Φ1 with respect to the x axis.

The use of such illumination lens 104 attains illumination having parallel light in the x direction and the angle Φ1 of around 45 degrees. A method for manufacturing the illumination lens 104 having a conic curved surface is described in U.S. Pat. No. 3,566,589, and therefore the explanation is omitted herein.

(3) Configuration for Attaining Three Beam Spots

Figure 5:
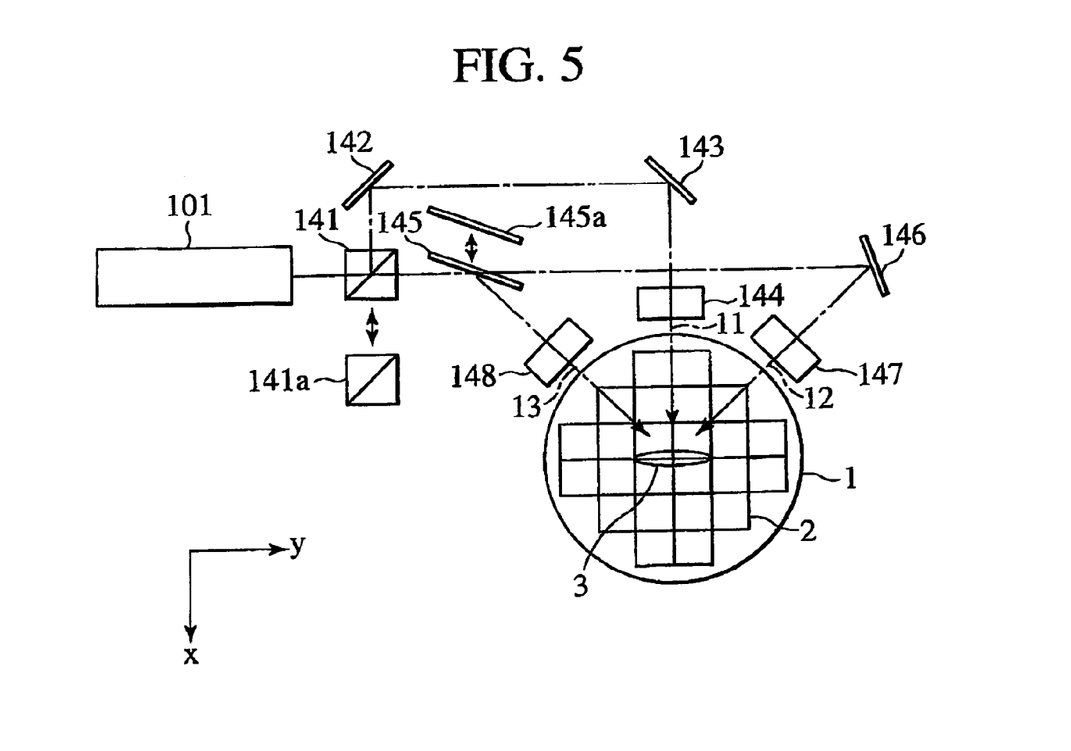
FIG. 5 explains an example of the structure of three beam-spot imaging units formed in the illumination optical system of the defect inspection system.

An example structure of the three beam-spot imaging units 110, 120 and 130 of the illumination optical system 100 will be explained below with reference to FIG. 5. The laser beam emitted from the laser light source 101 is branched into two optical paths (light beams) by a first branch optical element 141 such as a half mirror. One branch light beam reflects off mirrors 142 and 143 and then enters a concave lens 144 constituting the first beam-spot imaging unit 110 to generate the illumination light beam 11 from the first beam-spot imaging unit 110. The other branch light beam is further branched into two optical paths (light beams) by a second branch optical element 145 such as a half mirror. One branch light beam reflects off a mirror 146 and then enters a concave lens 147 constituting the second beam-spot imaging unit 120 to generate the illumination light beam 12 from the second beam-spot imaging unit 120. The other branch light beam enters a concave lens 148 constituting the third beam-spot imaging unit 130 to generate the illumination light beam 13 from the third beam-spot imaging unit 130.

When the first branch optical element 141 is removed or replaced with a pass-through optical element 141a, the illumination light beam 11 from the first beam-spot imaging unit 110 is not generated. Specifically, only the illumination light beam 12 from the second beam-spot imaging unit 120 and the illumination light beam 13 from the third beam-spot imaging unit 130 are generated. When the first branch optical element 141 is removed or replaced with the pass-through optical element 141a and further the second branch optical element 145 is replaced with a mirror 145a, only the illumination light beam 13 from the third beam-spot imaging unit 130 is generated. When the first branch optical element 141 is removed or replaced with the pass-through optical element 141a and further the second branch optical element 145 is removed or replaced with a pass-through optical element, only the illumination light beam 12 from the second beam-spot imaging unit 120 is generated.

When the first branch optical element 141 is disposed and the second branch optical element 145 is replaced with the mirror 145a, only the illumination light beam 11 from first beam-spot imaging unit 110 and the illumination light beam 13 from third beam-spot imaging unit 130 are generated. When the first branch optical element 141 is disposed and the second branch optical element 145 is removed or replaced with an pass-through optical element, only the illumination light beam 11 from the first beam-spot imaging unit 110 and the illumination light beam 12 from the second beam-spot imaging unit 120 are generated.

In this way, the present embodiment can generate any one of the illumination light beams 10, 11, and 12 from the three beam-spot imaging units 110, 120 and 130, respectively.

(4) Upright Detector

The upright detector 200 will be explained below. When the substrate (sample) 1 is radiated with a testing illumination light beam and the slit-like beam spot 3 is generated, a reflection light beam containing scattered light is emitted. This output light beam is emitted from the transparent thin film top surface, undersurface, and a circuit pattern, and a defect such as a particle on the substrate. The output light passes through the detection lens 201, the spatial filter 202, and the imaging lens 203 of the upright detector 200, and then is received by the sensor 205 to be subjected to photoelectric conversion therein. The luminance (power) of a light flux from the laser light source 101 can be changed through control of an ND filter 104 or the laser power, making it possible to change the dynamic range of the output of the sensor 205.

(5) Spatial Filter

The spatial filter 202 will be explained below. When a repetitive pattern on the sample is radiated with a testing illumination light beam, a diffracted-light strip (diffracted interference light strip) is generated. If the diffracted-light strip is received by the sensor 205, an error signal is generated making it impossible to detect a defect such as a particle. In order to intercept a Fourier transform image caused by the diffracted light from the repetitive pattern, the spatial filter 202 is disposed in a spatial frequency region of the objective lens 201, i.e., at an imaging position of Fourier transform (equivalent to an emission iris).

Normally, a light-shielding pattern of the spatial filter 202 is set so as to eliminate the diffracted light from a frequent repetitive pattern. The spatial filters 202 described in JP-A-5-218163 and JP-A-6-258239 include a structure that allows the light-shielding pattern to be changed. A plurality of different light-shielding patterns may be prepared as the spatial filter 202. In any case, the diffracted light can be intercepted by changing or switching the light-shielding pattern according the circuit pattern.

As mentioned above, when a concave portion between linear patterns is irradiated with the testing illumination light beam 11 which is along the x-axis direction, it is necessary to intercept the 0th-order diffracted light by using the spatial filter 202. The spatial filter 202 may be configured to intercept not only the 0th-order diffracted light but also a high-order diffracted light be intercepted.

(6) Adjustment of the Detection Sensitivity in the Upright Detector

A method for adjusting the detection sensitivity in response to the size of a defect such as a particle to be detected will be explained below. When the pixel size on the substrate (sample) 1 of the one-dimensional sensor (image sensor) 205 such as a TDI sensor is decreased, a smaller defect such as a particle can be detected although throughput is degraded. Three different detectors 200 are provided to attain variable image size on the substrate (sample) with respect to the pixel of the one-dimensional sensor (image sensor) 205. For example, in order to detect a defect such as a particle having a size of about 0.1 micrometers or less, the detector 200 which decreases the pixel size on the substrate (sample) 1 is selected. As a method for attaining such a configuration, an appropriate lens in a lens group 204 is selected. For example, it is preferable to design the lenses configuration so that the length of the optical path from the substrate (sample) 1 to the one-dimensional sensor 205 such as a TDI sensor remains unchanged. When designing of lenses configuration is difficult, it is possible, of course, along with the above-mentioned lens switching, to use a mechanism which can change the distance to the sensor. It is also possible to select an appropriate sensor different in pixel size from the other.

(7) Oblique Detector

Figure 6:
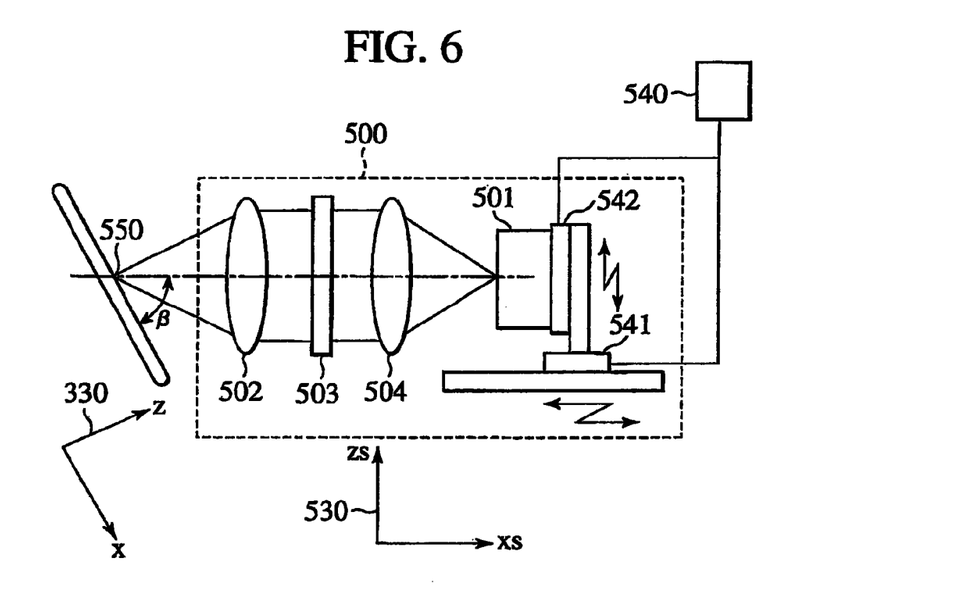
FIG. 6 shows the structure of an oblique detector in the defect detection system.

Then, the oblique detector 500 will be explained below with reference to FIG. 6. The optical axis of the oblique detector 500 is inclined with respect to the sample surface by a predetermined angle β. As described in JP-A-2007-107960, in order to reduce the amount of scattered light detected from the undersurface of the transparent thin film, it is necessary to arrange the optical axis of the oblique detector 500 so as to detect an output light having an output angle ranging from about 80 to about 90 degrees.

The light from a slit-like beam spot formed on the sample passes through the objective lens 502, the spatial filter 503, and the imaging lens 504, and then is detected by the one-dimensional sensor (image sensor) 501. The present embodiment uses a one-dimensional sensor (image sensor) in order to detect the image of the slit-like beam spot. The spatial filter 503 intercepts the diffracted-light strip (diffracted interference light strip) from the repetitive pattern on the sample in the same way as the spatial filter 202 of the upright detector 200.

The optical axis of the oblique detector 500 is inclined with respect to the wafer surface by an elevation angle β. Then, a coordinate system for describing the oblique detector 500 will be defined. The above-mentioned coordinate system is rotated counterclockwise around the y axis in the xz plane, which is defined as an oblique coordinate system 530 having the xs, ys, and zs axes. The ys axis is perpendicular to the paper surface and therefore not shown. The oblique coordinate system 530 is shown in FIG. 6. According to the oblique coordinate system 530, the main optical axis of the detector 500 is in parallel with the xs axis, and the longitudinal direction of the one-dimensional sensor 501 is in parallel with the ys axis.

The one-dimensional sensor 501 is driven by single-axis stages 541 and 542 which move in the xs- and zs-axis directions, respectively, in the oblique coordinate system 530. These single-axis stages 541 and 542 are controlled by a stage controller 540.

(8) Correcting the Detection Sensitivity of the Oblique Detector

Figure 7:
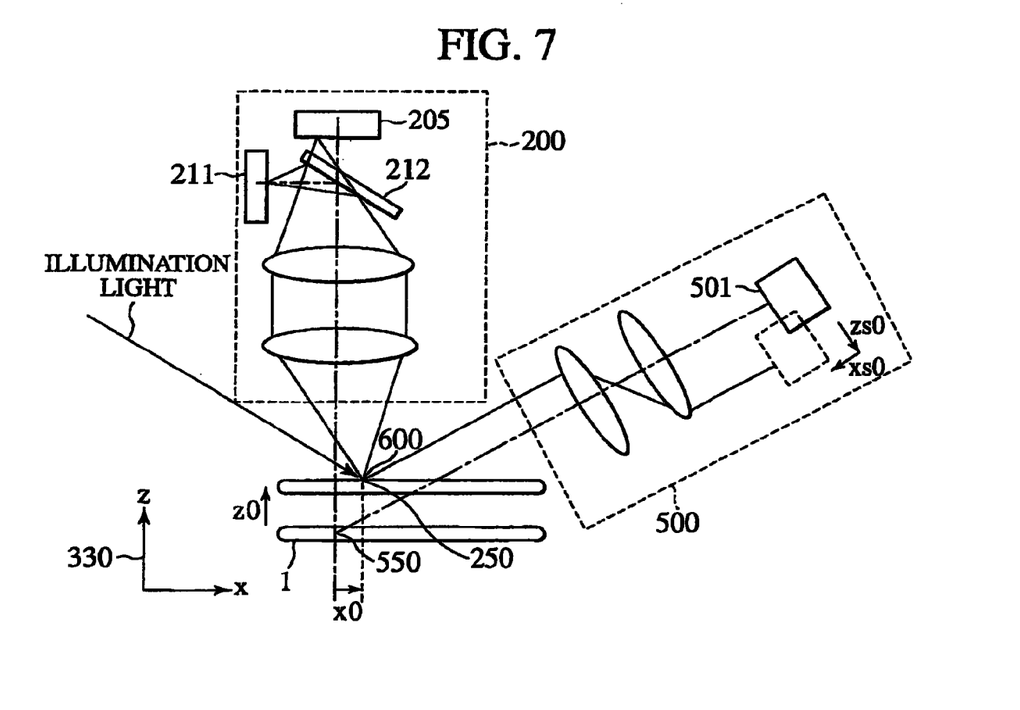
FIG. 7 shows a relation between an upright detector and an oblique detector in the defect detection system.

A beam irradiation position 600 (equivalent to the beam spot 3 of FIG. 2) is detected by a beam position sensor 211 provided in the upright detector 200 as shown in FIG. 7. The sensor 211 is a CCD sensor optically having the same imaging position as the one-dimensional sensor 205 by use of an optical branch element 212 (or mirror) such as a half mirror. The sensor 211 is used to ensure that the beam be appropriately applied within the field of the one-dimensional sensor 205. This makes it possible to obtain the x coordinate (in the coordinate system 330) of the illumination position of the beam to the wafer. The sensor 211 may be not only a CCD sensor but also a 2D sensor or a one-dimensional sensor arranged so as to obtain the beam position.

The reason for the degradation of the detection sensitivity of the oblique detector 500 will be explained below. In the upright detector 200, the focal length of the objective lens changes due to changing of temperature or atmospheric pressure. Accordingly, the wafer height is changed to correct the focal length. When the wafer height and the beam illumination position 600 are moved so as to be aligned with the field of view 250 of the upright detector 200 (overlapped with the beam irradiation position) in this way, a gap arises between the detection field of view 550 of the oblique detector 500 and the detection field of view 250 of the upright detector 200. Because of the above alignment, the imaging position of the scattered light from the wafer in the oblique detector 500 deviates from the position of the one-dimensional sensor 501, as shown in FIG. 7, resulting in detection of a defocused image and degraded detection sensitivity. Specifically, since the scattered light is detected by the oblique detector 500, the image at which the beam is irradiated is imaged.

As mentioned above, a defect inspection system using a plurality of detectors has a problem such that, when a position of an object to be tested is aligned with the inspection field of view of one detector, the detection sensitivity of other remaining detectors is degraded.

With the present embodiment, if the position of the one-dimensional sensor 501 of the oblique detector 500 is moved so that the detection field of view 250 coincides with the detection field of view 550, the scattered light from the wafer is appropriately imaged on the one-dimensional sensor 501, thus preventing the detection sensitivity from degrading. Although it is desirable that the detection field of view 250 completely coincides with the detection field of view 550, an appropriate permissible value can be provided depending on the pixel size of the one-dimensional sensor 550 and the one-dimensional sensor 250 and on the focal depth of the upright detector 200 and oblique detector 500.

Figure 8:
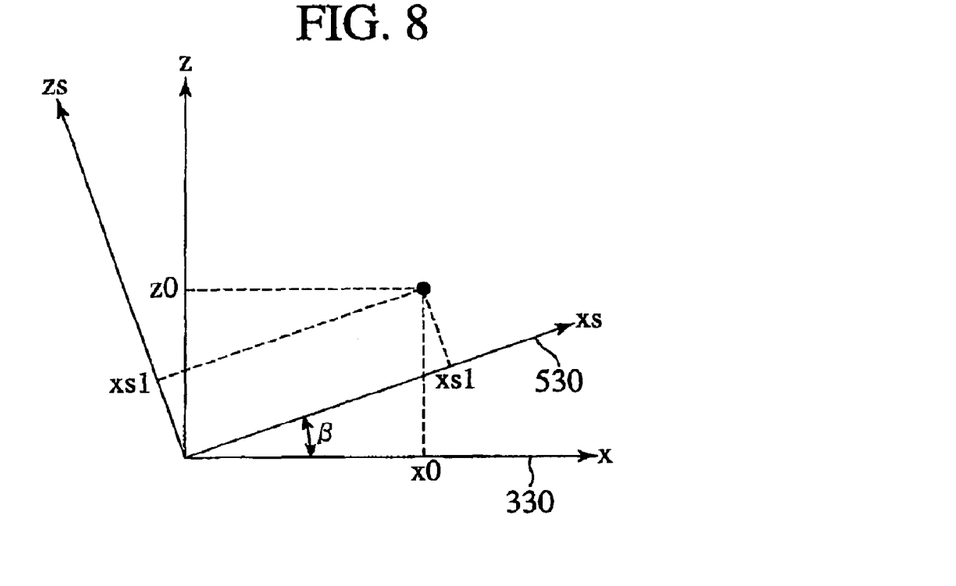
FIG. 8 shows a relation between the coordinate system in the defect detection system and an oblique coordinate system.

The above will be reconsidered with reference to coordinate systems. As shown in FIG. 8, an appropriate particle position when the one-dimensional sensor is disposed at its original position is defined as an origin (0,0). At this time, the coordinate (in the coordinate system 330) of an illuminated particle when the wafer height or the illumination position is changed due to the above-mentioned reason is defined as (x0, z0). If the coordinate (in the oblique coordinate system 530)

of the particle is defined as (xs1, zs1), the following formulas (1) and (2) are obtained through simple coordinate conversion as shown in FIG. 8.

$$xs1 = x0 \cdot \cos\beta + z0 \cdot \sin\beta \quad (1)$$

$$zs1 = -x0 \cdot \sin\beta + z0 \cdot \cos\beta \quad (2)$$

When the single-axis stage 541 and 542 are driven to move the one-dimensional sensor 501 in accordance with the coordinate (in the oblique coordinate system 530) of the particle obtained by the formulas (1) and (2), an image of the particle in focus can be detected, thus preventing the defect detection sensitivity from degrading.

Further, correction of detection sensitivity may be performed even if an error arises for each condition by correcting the detection sensitivity for each condition such as the magnification of the optical system, the elevation angle of illumination, and the like.

The defect inspection system of the present embodiment is applicable also to a method for reducing machine-to-machine difference. Specifically, when the detection field of view 250 does not coincide with the detection field of view 550 or when a positional variation arises for each inspection condition, because of differences in optical characteristics between the upright detector 200 and the oblique detector 500 or differences between parts, machine-to-machine difference can be corrected by adjusting the positions of the above-mentioned detectors.

Although the present embodiment is provided with two detectors, the upright detector and the oblique detector, the present invention is not limited thereto and a plurality of oblique detectors may be installed. Even in a case where a plurality of oblique detectors are provided, correction of the imaging position in all the oblique detectors may be performed according to the amount of movement of the wafer by adjusting the height of the substrate (wafer) 1 to adjust the detection field of view of the upright detector.

Further, it is not necessary that the optical axis of the upright detector exists on the normal line of the substrate (wafer) 1. Specifically, when the imaging position of one detector in a plurality of detectors is adjusted, if the imaging positions of other remaining detectors shift by the imaging position adjustment, the imaging positions of the other remaining detectors are relatively adjusted in relation to the amount of adjustment of the one detector. The amount of relative adjustment is calculated based on the same concept as in formulas (1) and (2).

(9) Concrete Method for Attaining Sensor Position Correction

Figure 9:
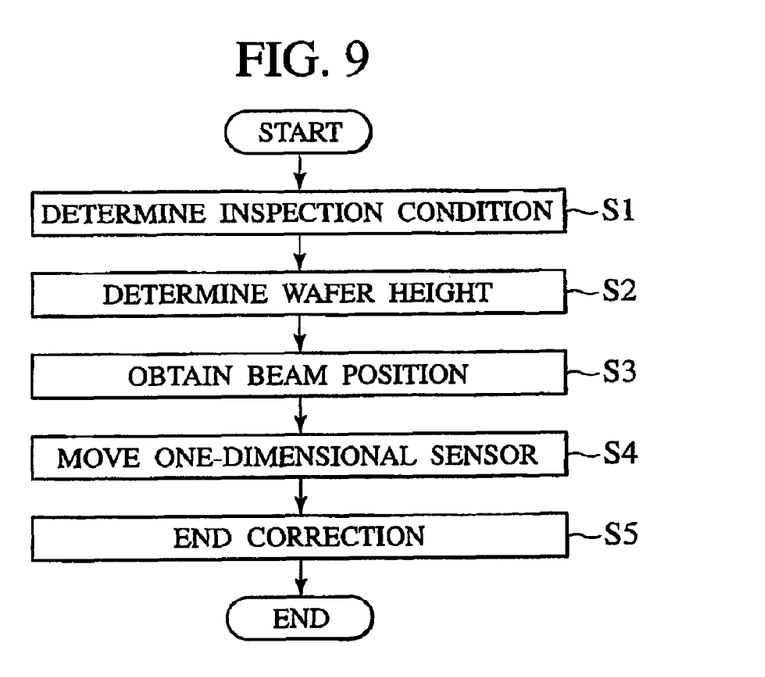
FIG. 9 is a flow chart for explaining the processing for correcting the sensor position of the oblique detector in the defect detection system.

A flow of positional correction of the one-dimensional sensor 501 will be explained below. FIG. 9 is a flow chart for explaining positional correction processing of the one-dimensional sensor 501.

First, in Step S1, the calculation and processing unit 401 determines inspection conditions such as the magnification of detectors, the elevation angle of the illumination system, and the like. For example, the calculation and processing unit 401 obtains from a memory (not shown) inspection conditions associated with a desired throughput value, the wafer type, etc., which are input from the input unit 404.

In Step S2, the calculation and processing unit 401 determines the height of the wafer 1 in relation to the upright detector 200 to cope with the variation in the focal length of the upright detector 200. At this time, the wafer height is detected as z0 by the calculation and processing unit 401.

In Step S3, the optical branch element 212 and a sensor 211 detect the beam illumination position 600 on the wafer 1. The calculation and processing unit 401 obtains information about the detected beam irradiation position 600. At this time, the beam irradiation position 600 is detected as x0 by the calculation and processing unit 401.

In Step S4, the calculation and processing unit 401 corrects the position of the one-dimensional sensor 501 based on x0 and z0 obtained in Steps S3 and S2, respectively. Specifically, the calculation and processing unit 401 calculates the positions xs1 and zs1 to be corrected, using the formulas (1) and (2), and then moves the sensor position by means of the single-axis stages 541 and 542 to correct the position of the one-dimensional sensor 501.

When the above processing is performed, the sensor positions can be appropriately corrected for each inspection condition, thus preventing the detection sensitivity of the oblique detector 500 from degrading. Further, the effect of reducing machine-to-machine difference caused by an optical system having variation for each machine is also enhanced.

It may also possible to adjust the sensor position of the upright detector in relation to the focal position of the oblique detector.

In accordance with the defect inspection system of the present invention, making a detection field of view of one detector coincide with a detection field of view of the other detector, thus preventing the defect detection sensitivity from degrading.

While the invention has been described in its preferred embodiments, it is to be understood that the words which have been used are words of description rather than limitation and that changes within the purview of the appended claims may be made without departing from the true scope and spirit of the invention in its broader aspects.

What is claimed is:

1. A defect inspection system for inspecting a defect in a sample, the system comprising:
   a stage on which the sample is moved;
   an illumination optical system for irradiating a surface of the sample with a testing illumination light beam having a predetermined incident angle with respect to the sample surface to generate a beam spot on the sample surface;
   an oblique detector including a first sensor having a first optical axis inclined with respect to the sample surface by a predetermined angle to detect light from the beam spot, and a sensor movement device which moves the first sensor;
   an upright detector including a second sensor having a second optical axis along the normal of the sample surface to detect light from the beam spot; and
   a signal processor including a processing controller to detect a defect on the sample using outputs from the oblique detector and the upright detector;
   wherein the processing controller controls the stage to move the sample in the second optical axis direction to adjust the focal length of the upright detector; and
   wherein the processing controller controls the sensor movement device according to the amount of movement of the sample to move the position of the first sensor in the oblique detector.

2. The defect inspection system according to claim 1, wherein:
   the processing controller calculates the coordinate (xs1, zs1) of a defect in the xz coordinate system of the oblique detector using the following formulas:

$$xs1 = x0 \cdot \cos\beta + z0 \cdot \sin\beta$$

$$zs1 = -x0 \cdot \sin\beta + z0 \cdot \cos\beta$$

and controls the sensor movement device so that the first sensor is disposed at an imaging position associated with the coordinate (xs1, zs1) of the defect,
where the coordinate of the defect before the sample is moved is (0, 0), the coordinate of the defect in the xz coordinate system of the upright detector is (x0, z0), the coordinate of the defect in the oblique xz coordinate system of the oblique detector is (xs1, zs1), and the oblique angle of the oblique detector is $\beta$.

3. The defect inspection system according to claim 1, wherein:
the illumination optical system generates a slit-like beam spot.

4. The defect inspection system according to claim 1, wherein:
the illumination optical system comprises:
a first illumination beam-spot imaging unit for irradiating a surface of the sample with a testing illumination light beam from a direction opposite to the oblique detector;
a second illumination beam-spot imaging unit for irradiating the sample surface with a testing illumination light beam from a direction inclined by a predetermined angle with respect to the direction of the testing illumination light beam from the first illumination beam-spot imaging unit; and
a third illumination beam-spot imaging unit for irradiating the sample surface with a testing illumination light beam from a direction inclined by a predetermined angle with respect to the direction of the testing illumination light beam from the second illumination beam-spot imaging unit;
wherein at least one of the first, second, and third illumination beam-spot imaging units is used to generate the beam spot.

5. The defect inspection system according to claim 1, wherein:
the sensor movement device in the oblique detector is composed of two single-axis stages that are adapted to move the first sensor in the x- and z-axis directions in the oblique xz coordinate system.

6. A defect inspection system for inspecting a defect in an object under inspection, the system comprising:
a stage on which the object under inspection is moved;
an illumination optical system for irradiating a surface of the object under inspection with a testing illumination light beam having a predetermined incident angle with respect to the surface of the object under inspection to generate a beam spot on the surface of the object under inspection;
a first detector including a first sensor having a first optical axis with respect to the surface of the object under inspection to detect light from the beam spot, and a sensor movement device which moves the first sensor;
a second detector including a second sensor having a second optical axis with respect to the surface of the object under inspection to detect light from the beam spot; and
a signal processor including a processing controller to detect a defect on the object under inspection using outputs from the first and second detectors;
wherein the processing controller controls the stage to move the object under inspection in the second optical axis direction to adjust the focal length of the second detector; and
wherein the processing controller controls the sensor movement device according to the amount of movement of the object under inspection to move the position of the first sensor in the first detector.

* * * * *